(12) United States Patent
Hartl et al.

(10) Patent No.: US 7,191,505 B2
(45) Date of Patent: Mar. 20, 2007

(54) SEALED SENSOR HOUSING AND METHOD OF MAKING

(75) Inventors: Helmut Hartl, Vienna (AT); Christian Bauer, Tulln (AT)

(73) Assignee: Electrovac AG, Klosterneuburg (AT)

( * ) Notice: Subject to any disclaimer, the term of this patent is extended or adjusted under 35 U.S.C. 154(b) by 0 days.

(21) Appl. No.: 11/038,794

(22) Filed: Jan. 20, 2005

(65) Prior Publication Data

US 2005/0121323 A1  Jun. 9, 2005

Related U.S. Application Data

(63) Continuation of application No. PCT/IB2004/001438, filed on Mar. 12, 2004.

(60) Provisional application No. 60/454,794, filed on Mar. 13, 2003.

(51) Int. Cl.
*B23P 11/00* (2006.01)
*B23P 25/00* (2006.01)
*H01S 4/00* (2006.01)
*G01N 27/26* (2006.01)

(52) U.S. Cl. .................. 29/432.2; 29/458; 29/592.1; 204/409

(58) Field of Classification Search .......... 29/432.2, 29/428, 458, 469, 705, 801, 283.5, 593, 507, 29/592.1, 506, 505; 204/409, 400, 193
See application file for complete search history.

(56) References Cited

U.S. PATENT DOCUMENTS

| 5,124,655 A | 6/1992 | Takeuchi et al. |
| 5,182,523 A | 1/1993 | Ertel et al. |
| 5,950,483 A * | 9/1999 | Schneider et al. ............ 72/414 |

FOREIGN PATENT DOCUMENTS

| JP | 63-243455 | 10/1988 |
| JP | 06-248973 | 9/1994 |
| JP | 07-167816 A | 7/1995 |
| WO | WO 02/093150 A1 | 11/2002 |

* cited by examiner

*Primary Examiner*—John C. Hong
(74) *Attorney, Agent, or Firm*—Christopher Paradies; Fowler White Boggs Banker P.A.

(57) ABSTRACT

A sealed sensor housing for use in measuring the concentration of an additive or impurity in gasoline comprises a housing body of metal formed by a deformation process with no substantial machining, and the housing body is joined together with an inlet tube, an outlet tube and an electrode such that the electrode is hermetically sealed in the housing body. The deformation process may be hydroforming, deep drawing, coldforming, forging or stamping.

18 Claims, 5 Drawing Sheets

SEALED SENSOR HOUSING AND METHOD OF MAKING

RELATED APPLICATION

This is a continuation of international application PCT/IB2004/001438, which was filed with the United States Patent and Trademark Office on Mar. 12, 2004 and received an international patent application serial number of PCT/US2004/007663, and which claims the benefit of U.S. Provisional Application No. 60/454,794, filed Mar. 13, 2003, which is incorporated in its entirety by reference herein.

FIELD OF THE INVENTION

The invention relates to a sealed sensor for measuring electrical conductivity of a liquid and a method for manufacturing the sensor using stamping, hydroforming and other deformation processes.

BACKGROUND OF THE INVENTION

FIG. 3 shows a conventional sensor for measuring the electrical conductivity of a fluid having a one-piece housing formed by casting and subsequent machining to the tolerances necessary for the sensor. The housing 30 is typically made of a castable metal alloy and requires thick walls to maintain a hermetic seal. The casting process introduces several undesirable limitations on the sensor. For example, metal alloys suitable for use in the casting of hermetically sealable enclosures may be inappropriate for use as an active part of the sensor, requiring the use of a second electrode as a reference. Cast parts typically have a greater percentage of porosity than parts made by deformation processing methods; therefore, wall thicknesses of cast parts must be greater than parts formed by deformation processing, such as stamping, deep drawing, hydroforming and coldforming. The unintentionally influence sensor measurements, causing an undesirable variation from sensor to sensor.

SUMMARY OF THE INVENTION

A sensor for measuring the concentration of an additive or impurity in a fluid comprises a body that is assembled from parts that are formed by deformation processing, for example hydroforming, stamping and coldforming. The parts are assembled and joined together, for example using brazing, soldering, welding, adhesive bonding or combinations of these, such that the body is hermetically sealable. At least one conductive electrode is inserted into the body and hermetically sealed, for example using hermetic glass sealing or hermetic epoxy sealing.

One object of the invention is to replace the cast metal alloys of the prior art sensor with a metal alloy capable of being used as an active component for detecting the electrical conductivity, the permeability or the capacitance through a liquid. For example, a portion of the body is formed by hydroforming using the same metal alloy that is used in forming the electrode. The portion of the body and the electrode are connected to a circuit that detects the characteristics, such as the permeability or dielectric constant of a liquid passing between them. For example, the circuit may compare a detected value, such as a voltage, a current permeability, a dielectric constant or a resistance, to a known value that relates to the concentration of an additive and/or an impurity such as a salt.

Another object of the invention is to reduce the cost for manufacturing the sensor for measuring the electrical conductivity of a fluid. Yet another object of the invention is to reduce the weight of the sensor. Still another object of the invention is to improve the flexibility of the design and manufacturing of new and modified sensors. Yet another object of the invention is to produce a sensor body for measuring the electrical conductivity of a liquid that is made of a material resistant to gasoline, for example, stainless steel.

Herein, hermetic and hermetically do not mean a completely air tight seal, but instead mean substantially sealed. Substantially sealed means that the seal is effective in a commercial sensor, such as a leak rate of less than $1\times10^{-5}$ cubic centimeter per second at one atm differential in a helium leak test for a gasoline sensor.

Other features and advantages of the present invention will become apparent from the following description of the invention, which refers to the accompanying drawings.

BRIEF DESCRIPTION OF THE FIGURES

For the purpose of illustrating the invention, representative embodiments are shown in the accompanying figures, it being understood that the invention is not intended to be limited to the precise arrangements and instrumentalities shown.

FIG. 1b shows an alternative embodiment of the embodiment shown in FIG. 1a.

FIG. 4b shows an alternative embodiment of the embodiment shown in FIG. 4a.

DETAILED DESCRIPTION OF PREFERRED EMBODIMENT

The present invention will now be described in detail for specific embodiments of the invention. These embodiments are intended only as illustrative examples and the invention is not to be limited thereto.

Figure 1A:
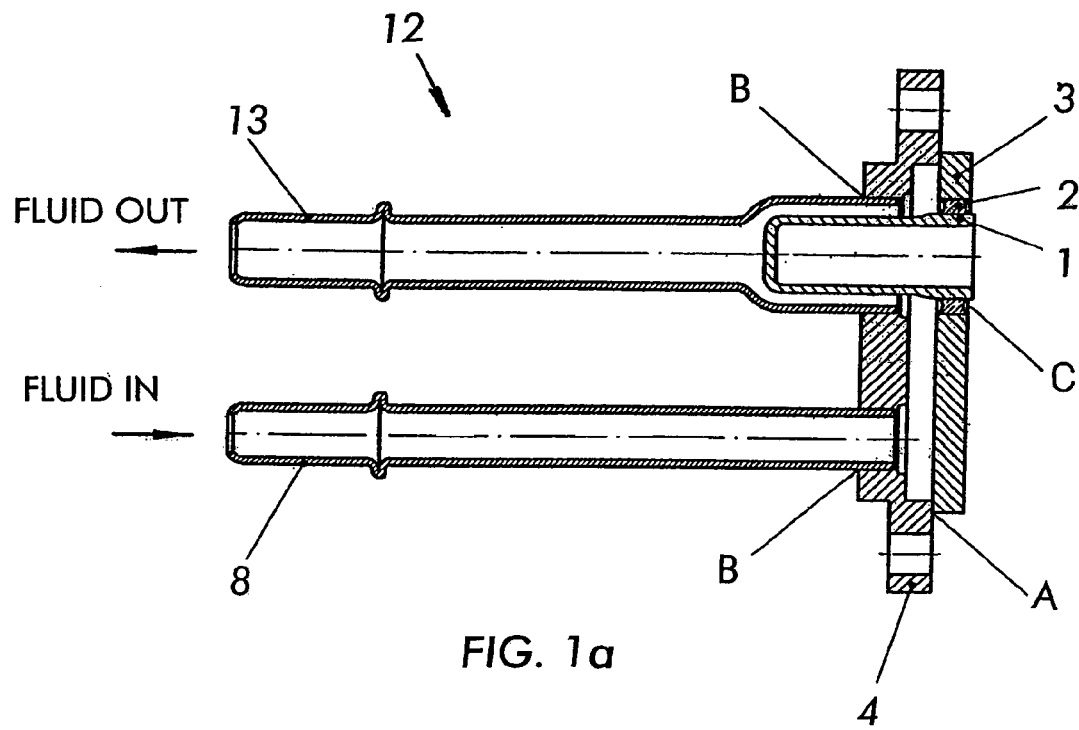
FIG. 1a shows one embodiment of the invention.
Figure 1B:
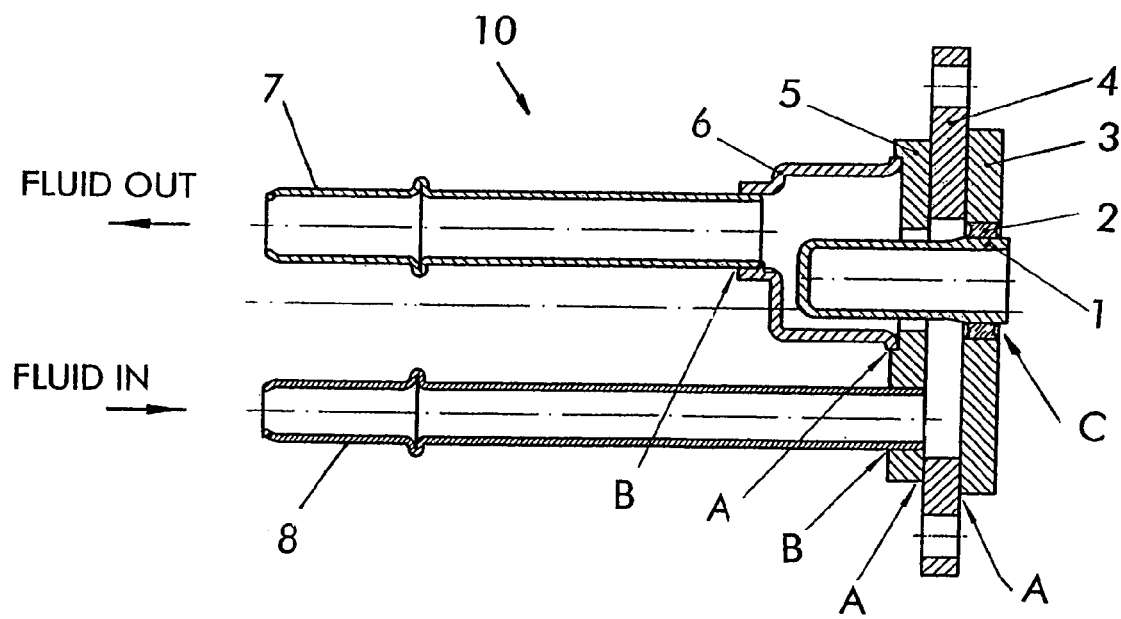

FIGS. 1a and 1b show alternative embodiments of the invention, having an electrode 1 inserted into the body of the sensor 10, 12 and hermetically sealed by the hermetic sealant 2 that seals between the electrode 1 and the base plate 3. The base plate 3 is joined A to a second plate 4. In an alternative embodiment, FIG. 1b, the second plate is a mid-plate 4 that is joined A to another plate 5. An upper electrode housing 6 is joined A to the top plate 5 in this alternative embodiment; however, FIG. 1a shows a one-piece housing 13 joined B directly to the second plate 4. Each of the base plate 3, the second plate 4 and the top plate 5 may be formed by any conventional deformation process; however, stamping of rolled sheet is a preferred process, which reduces cost and provides a good, tight seal. A tube 8 is sealed B to the body of the sensor 10 and functions as the inlet for the fluid. Another tube 7 is used in FIG. 1b. The electrode housing 6, 13 may be made by deep drawing, hydroforming, coldforming or any other deformation process known in the art.

The base plate 3, second plate 4, the top plate 5, the electrode housing 6, 13, the first tube 7 and the second tube 8 may be made of stainless steel. In another example, only the tubes 7, 8 and the housing 13 of FIG. 1a are made of stainless steel. Alternatively, the individual parts that make up the body of the sensor 10 may be any suitable material, such as a composite, a glass, a metal, a ceramic and/or an organic material. Preferably, the material is a hermetic material, such as an hermetic metal. An hermetic metal means a metal that is capable of being hermetically sealed, such that the hermetically sealed metal meets or exceeds a specific leak tightness necessary for operation of the sensor. For example, the sensor housing of FIG. 1b has a leak rate of less than $1\times10^{-5}$ cubic centimeters per second at one atmosphere differential, as determined by a helium leak test using a mass spectrometer. More preferably, the leak rate is less than $10^{-7}$ cubic centimeters per second. The hermetic sealant may be any sealable material, such as a borosilicate glass, a glass filled ceramic or an epoxy. For example, Pave epoxy seals are available from PAVE Technology of Dayton, Ohio.

Figure 2:
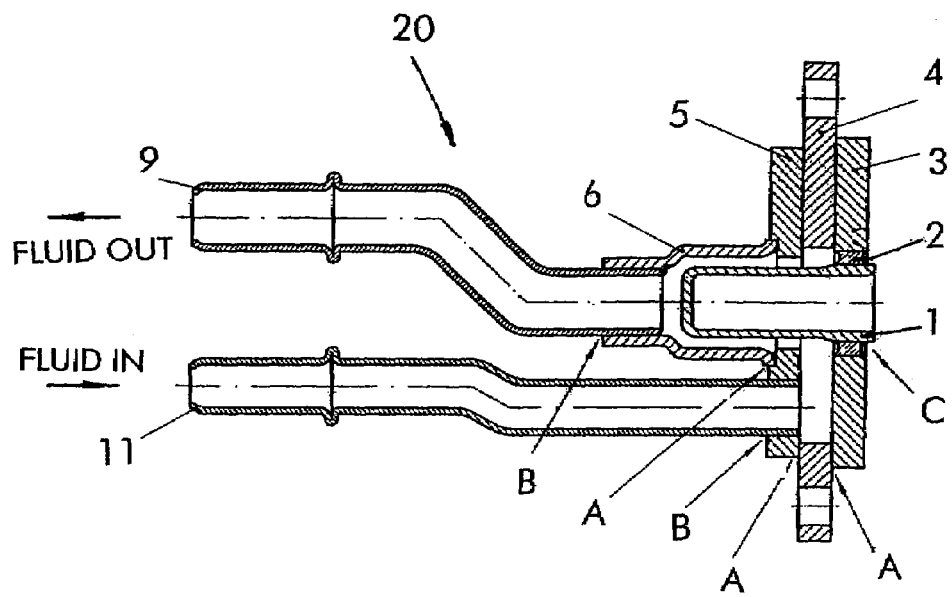
FIG. 2 shows another embodiment of the invention.

In FIG. 2, another embodiment of the invention is shown having an electrode 1 centered in an electrode housing 6. The first tube 9 and the second tube 11 are bent, such that the body of the sensor 20 may be used to replace an existing conventional sensor, such as that shown in FIG. 3. Otherwise, the example is similar to the example illustrated in FIG. 1b and the same reference numbers and letters are used to identify similar features.

Figure 3:
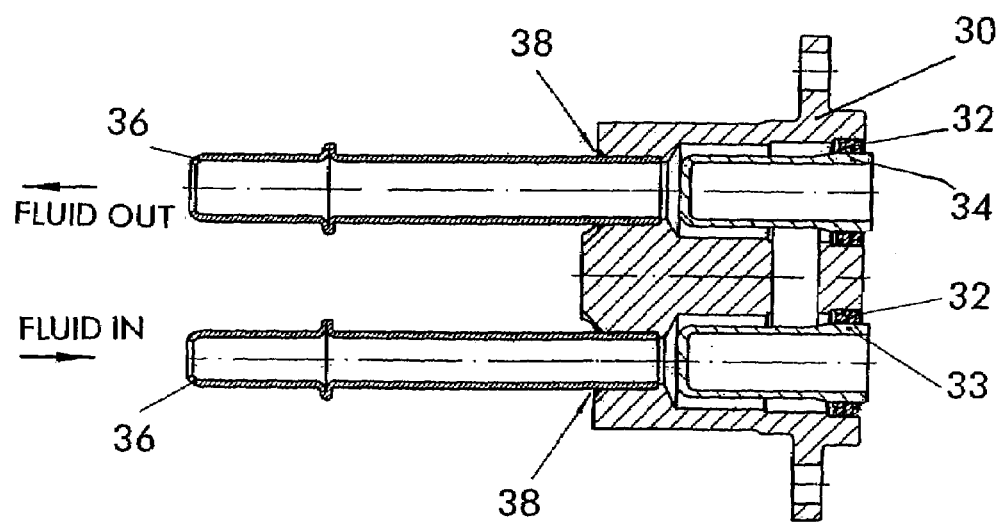
FIG. 3 shows a hermetically sealed sensor of the prior art.

The conventional sensor of FIG. 3 has two electrodes, 33 and 34, inserted into a cast housing 30 that has been machined to have two cavities to accommodate the first electrode 34 and the second electrode 33. The sensor of FIG. 3 is heavier and more costly to produce than the sensors of FIGS. 1 and 2. The inlet and outlet tubes 36 are joined to the housing 30.

Figure 4A:
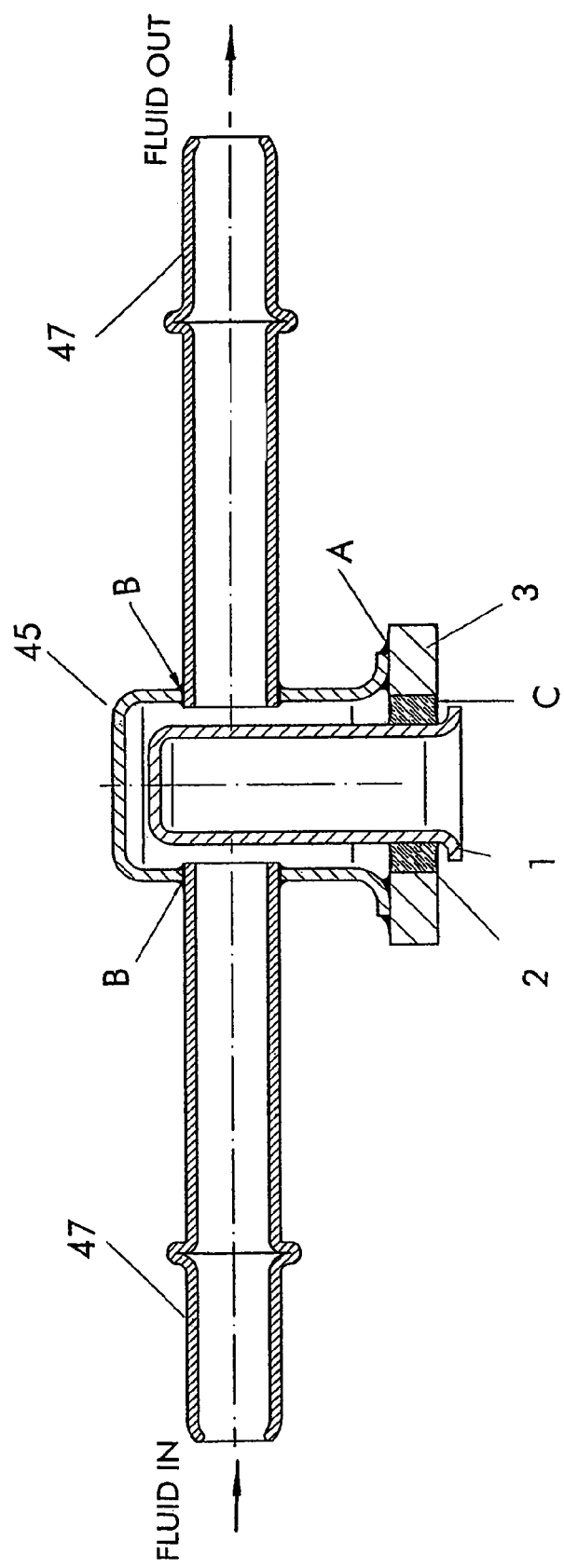
FIG. 4a shows another embodiment of the invention.
Figure 4B:
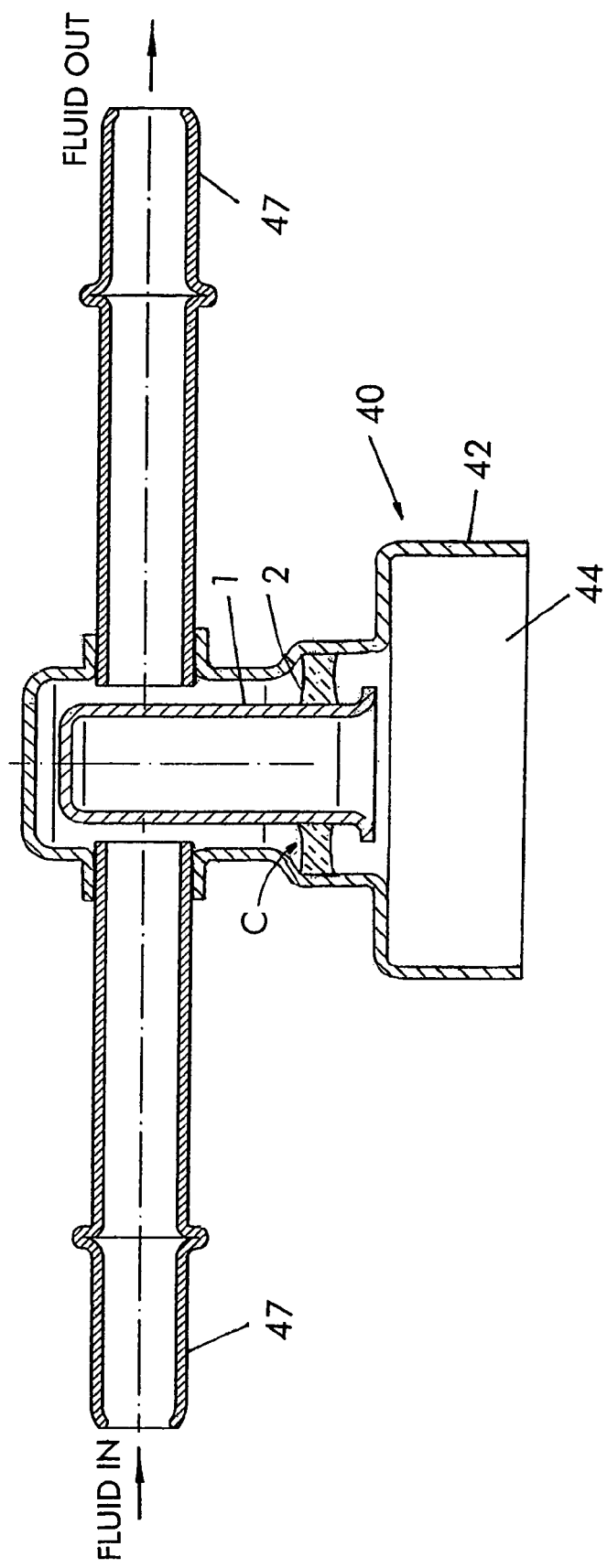

FIGS. 4a and 4b show another pair of alternative embodiments. In FIG. 4b, the body of the sensor 40 comprises an electrode housing 42, which may be hydroformed, for example. The housing 42 is coupled to two opposing inlet/outlet tubes 47. An electrode 1 is sealed C by an hermetic sealant 2 in the body of the housing 40. The lower portion 44 of the body 40 is formed by the hydroforming process that forms the electrode housing 42. The lower portion 44 is thus integrally joined to the electrode housing 42 and may be used as a cover for the electronics that detect the electrical characteristics of the fluid that is used to determine the concentration of additives or impurities in the fluid during the fluids transit between the electrode and the electrode housing. In FIG. 4a, a base plate 3 is sealed A directly to an electrode housing 45, which may be formed by deformation processes, such as hydroforming, for example. In the alternative shown in FIG. 4a, the base plate 3 may be coupled to a cover (not shown) that protects the electronics of the sensor. Preferably, the base plate 3 is hermetically sealed C to the electrode housing 45 by soldering, welding, brazing or adhesive bonding. The inlet and outlet 47 are joined B to the housing 45.

Figure 5:
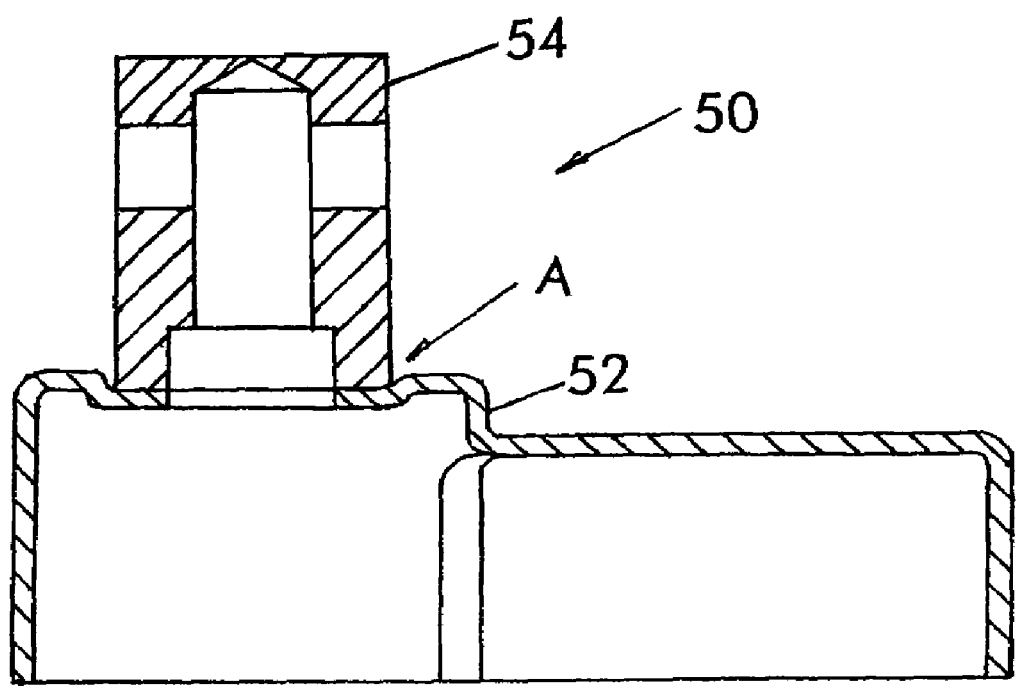
FIG. 5 shows yet another embodiment of the invention.

FIG. 5 shows another embodiment of the invention having a deep drawn base 52 joined A to an upper portion 54, which may be manufactured conventionally, to form the body of a housing 50. The sensor in FIGS. 4a and 4b is lighter weight and less expensive to manufacture than a sensor fabricated from the housing shown in FIG. 5, which requires machining of housing 54 and, hence, thicker walls.

The process of fabricating a sensor comprises forming each of the housing parts, for example a stamped base plate, a stamped second plate, a stamped top plate and an electrode housing formed using a deformation process such as deep drawing, hydroforming, forging and coldforming. The parts are then assembled and joined together into a sensor body that is capable of being hermetically sealed. For example, the parts are welded, brazed, soldered or adhesively bonded. An electrode is inserted into a portion of the housing body that forms an electrode housing. The electrode is hermetically and insulatingly sealed in the housing body such that no electrical contact is made between the electrode and the body. Inlet and outlet lines are attached to the sensor body. Optionally, the parts may be plated to resist corrosion from the liquid that will be in contact with the surfaces of the sensor body. In an alternative embodiment, the sensor body is formed by hydroforming. In a preferred embodiment, the joints between each of the individual housing parts are hermetically sealed, operably preventing unacceptable leakage as measured by a helium leak test.

Various deformation processes may be used to fabricate a one-piece sensor body or each of the individual parts of a multi-component body with substantially no machining. "Substantially no machining" means that machining is not used to shape the exterior or interior surfaces of the housing, but permits insubstantial machining operations such as burr removal, fitting of inlet and outlet tubes and correction of minor blemishes for fit and finish, as is known in the art. The choice of deformation processes, such as stamping, deep drawing, hydroforming and/or coldforming, is determined by the device specifications, including cost, compatibility with other materials, resistance to the fluid for which electrical conductivity measurements are desired and the accuracy desired for the electrical conductivity measurement. In one embodiment, a sensor detects the electrical conductivity (or alternatively, the resistivity), the permeability or the capacitance of gasoline. In this embodiment, each of the parts of the sensor body 10, 12, 20, 41 and 40, are steel, preferably stainless steel, or the parts are plated with a material resistant to the liquid, such as by adding a layer of a chrome, a nickel or an alloy of these and other elements.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A sealed sensor housing for use in detecting a concentration of an impurity or additive in a fluid, the housing comprising:

a housing body of a metal formed by a deformation process with substantially no machining, the housing body being joined to an inlet tube, an outlet tube, and an electrode, and wherein the housing body comprises:

a flat plate, the flat plate having a top surface, a bottom surface opposite of the top surface and a hole, the distance between the top surface and the bottom surface defining a thickness of the flat plate, the hole extending through the thickness of the flat plate;

a top plate having a top surface, a bottom surface opposite of the top surface of the top plate, an inlet hole and an outlet hole, the distance between the top surface and the bottom surface of the top plate defining a thickness of the top plate, the inlet hole and the outlet hole extending through the thickness of the top plate and being laterally displaced one from the other;

the top plate being coupled to the flat plate, hermetically, such that a channel is defined between the top plate and the flat plate for channeling the fluid from the inlet hole to the outlet hole; the electrode being sealed hermetically and insulatively by a hermetic sealant in the hole of the flat plate; and an electrode housing joined hermetically in one of the inlet hole or the outlet hole, the electrode housing aligning over the hole in the flat plate such that the electrode extends through the hole in the flat plate and into the electrode housing without contacting the electrode housing.

2. The housing of claim 1, wherein the electrode housing is joined hermetically in the outlet hole.

3. The housing of claim 2, wherein the inlet tube is joined hermetically in the inlet hole.

4. The housing of claim 3, wherein the outlet tube is integrally joined to the electrode housing.

5. The housing of claim 3, wherein the housing body further comprises a mid-plate joining the flat plate and the top plate, the mid-plate defining the channel between the flat plate and the top plate.

6. The housing of claim 5, wherein the outlet tube has a first and an opposite end, the first end being joined hermetically to the electrode housing.

7. The housing of claim 6, wherein the electrode housing is centered in the housing, and the outlet tube is formed such that the opposite end is offset radially from the center of the housing.

8. The housing of claim 1, wherein the electrode is sealed in the flat plate using an electrically insulating epoxy.

9. A sealed sensor housing for use in detecting a concentration of an impurity or additive in a fluid, the housing comprising:

a housing body of a metal formed by a deformation process with substantially no machining, the housing body being joined to an inlet tube, an outlet tube, and an electrode; and the housing body comprises:

an electrode housing, the electrode being displaced from the electrode housing forming a gap between the electrode and the electrode housing; and an inlet through one side of the electrode housing: and an outlet through another side of the electrode housing spatially displaced from the inlet such that the fluid passes between the electrode and the electrode housing; and the electrode is hermetically sealed to the electrode housing using an electrically insulating epoxy to fill the gap between a first portion of the electrode and a portion of the electrode housing adjacent to the first portion of the electrode, wherein the first portion of the electrode is disposed at a distance from each of the inlet and the outlet.

10. The housing of claim 9, wherein the housing body further comprises a cover integrally joined to the electrode housing and extending a surface of the electrode housing beyond the electrically insulating epoxy.

11. The housing of claim 9, wherein the distance between the first portion of the electrode and the inlet is greater than the distance between the outlet and the first portion of the electrode.

12. A method of making a sealed sensor comprising:

stamping a flat plate such that the flat plate has a hole through the flat plate;

forming an electrode having a closed end, an open end and elongated sidewalls between the closed end and the open end using deformation processing;

forming a housing for the electrode using deformation processing such that the electrode fits into the housing without electrically contacting the housing;

joining the flat plate and the housing;

inserting the electrode through the hole in the flat plate; and sealing the electrode using an electrically insulating sealant between a portion of the electrode and the flat plate, such that the electrode is sealed in the housing and no portion of the electrode makes electrical contact with any portion of the flat plate and the housing.

13. The method of claim 12, further comprising:

stamping a top plate having an inlet and an outlet; and prior to the step of joining, imposing the top plate between the flat plate and the housing.

14. The method of claim 13, wherein the top plate directly contacts the flat plate and the step of stamping the top plate forms a discontinuity in a surface of the top plate such that, after the steps of imposing and joining, a channel is defined by the opposing surfaces of the top plate and the flat plate between the inlet and the outlet.

15. The method of claim 13, further comprising:

stamping a mid-plate; and prior to the step of joining, imposing the mid-plate between the top plate and the flat plate; such that the mid-plate defines a channel between top plate and the flat plate from the inlet to the outlet after the step of sealing.

16. The method of claim 12, wherein the steps of sealing and joining seal the sensor hermetically.

17. The method of claim 12, wherein the step of forming the housing uses deep drawing, coldforming, or hydroforming.

18. The method of claim 17, wherein the step of forming the housing uses hydroforming.

* * * * *